United States Patent [19]

Yamamoto

[11] Patent Number: 5,965,176
[45] Date of Patent: Oct. 12, 1999

[54] METHOD OF MANUFACTURING A PROTEIN GEL

[75] Inventor: Yoshihisa Yamamoto, Kanagawa, Japan

[73] Assignee: Tetra Laval Holdings & Finance, S.A., Switzerland

[21] Appl. No.: 08/693,279

[22] PCT Filed: Feb. 20, 1995

[86] PCT No.: PCT/JP95/00236

§ 371 Date: Aug. 15, 1996

§ 102(e) Date: Aug. 15, 1996

[87] PCT Pub. No.: WO95/23524

PCT Pub. Date: Sep. 8, 1995

[30] Foreign Application Priority Data

Mar. 4, 1994 [JP] Japan .................................. 6-034786

[51] Int. Cl.$^6$ ........................................................ A23L 1/20
[52] U.S. Cl. .............................. 426/46; 426/44; 426/573; 426/634
[58] Field of Search ................................ 426/44, 46, 573, 426/574, 615, 629, 634

[56] References Cited

U.S. PATENT DOCUMENTS

| | | | |
|---|---|---|---|
| 4,303,678 | 12/1981 | Ogasa et al. .............................. | 426/46 |
| 4,664,919 | 5/1987 | Yan et al. .................................. | 426/46 |
| 4,917,904 | 4/1990 | Wakemada et al. ........................ | 426/7 |
| 4,988,519 | 1/1991 | Takenawa et al. ......................... | 426/63 |
| 5,055,310 | 10/1991 | Nonaka et al. ............................ | 426/46 |
| 5,156,956 | 10/1992 | Motoki et al. ....................... | 426/573 X |

*Primary Examiner*—Leslie Wong
*Attorney, Agent, or Firm*—Lorusso & Loud

[57] ABSTRACT

A method of manufacturing a protein gel. In the first step, a protein-containing solution is heated for sterilization. In the second step, the protein-containing solution is cooled, and an enzyme is added to the protein-containing solution. In the subsequent third step, the protein-containing solution and the enzyme are mixed while maintaining the temperature in the second step so as to obtain a mixture. In the fourth step, the mixture is aseptically filled in a food container. In the fifth step, the aseptically filled mixture is allowed to stand at ambient temperature, during which the enzyme denatures the protein in the protein-containing solution. Since the mixture is not required to be heated for denaturing the protein in the protein-containing solution, the energy consumed in the manufacturing process is reduced, thereby lowering the manufacturing costs.

13 Claims, 6 Drawing Sheets

METHOD OF MANUFACTURING A PROTEIN GEL

This is a National Stage Filing of PCT/JP95/00236, filed Feb. 20, 1995.

TECHNICAL FIELD

The present invention relates to a method of manufacturing a protein gel.

BACKGROUND ART

In conventional methods of manufacturing a protein gel such as tofu (bean curd) in which an aqueous solution containing protein (hereinafter referred to as "protein-containing solution") is filled in a food container for curdling therein, a curdling chemical, transglutaminase or the like is added to the protein-containing solution, and is then heated.

FIG. 1 is a flowchart showing a first conventional method of manufacturing a protein gel, and FIG. 2 is a temperature profile in the first conventional method of manufacturing a protein gel. In FIG. 2, the abscissa represents time while the ordinate represents temperature.

As shown in FIGS. 1 and 2, in the first step, the temperature of a protein-containing solution is elevated from about 80° C. to a temperature of 130–140° C. at a time t1 to heat the solution for a few to 10 seconds for sterilization.

When the protein gel to be obtained is tofu, soymilk is used as the protein-containing solution. A process for manufacturing the soymilk is as follows. Soy beans are first washed and then immersed in an unillustrated immersion tank. Thereafter, the soy beans are crushed with an unillustrated grinder to obtain "go", a paste of crushed soy beans, which is then heated at a temperature of 98–105° C. for 2–5 minutes. Thereafter, tofu refuse is removed from the "go" to obtain soymilk.

In the second step, a curdling chemical is added to the protein-containing solution at a time t2. In this step, gluconodeltalactone (GDL), magnesium chloride ($MgCl_2$) or the like is used as the curdling chemical. The curdling chemical is added to the protein-containing solution after being passed through a bacteria-removing filter. The temperature of the protein-containing solution is maintained at 10° C. to prevent the chemical reaction from proceeding, which would otherwise occur at higher temperatures.

In the subsequent third step, the protein-containing solution is mixed with the curdling chemical at a time t3 to obtain a mixture. In this step, the temperature of the protein-containing solution is also maintained at 10° C. to prevent the chemical reaction from proceeding, which would otherwise occur at higher temperatures.

In the fourth step, the mixture is aseptically filled in an unillustrated food container at a time t4. In this step, the temperature of the protein-containing solution is maintained at 10° C. to prevent the chemical reaction from proceeding, which would otherwise occur at higher temperatures.

In the fifth step, the mixture is heated at a temperature of 90–95° C. for 30 minutes, at a time t5, for curdling the protein-containing solution in the mixture by the action of the curdling chemical.

A protein gel can be manufactured in this manner.

FIG. 3 is a flowchart showing a second conventional method of manufacturing a protein gel, and FIG. 4 is a temperature profile in the second conventional method of manufacturing a protein gel. In FIG. 4, the abscissa represents time while the ordinate represents temperature.

As shown in FIGS. 3 and 4, in the first step, a protein-containing solution is cooled from about 80° C. to a temperature of 25–50° C. at a time t11. To a cooled solution, transglutaminase is added. Transglutaminase is an enzyme serving as a catalyst in an acyl transferring reaction of a Y-carboxyamide group, which is a glutamine residue in a peptide chain.

In the second step, the protein-containing solution is mixed with transglutaminase at a time t12. In this step, the temperature of the protein-containing solution is maintained at 25–50° C. to prevent the catalytic reaction from proceeding by the presence of transglutaminase, which would otherwise occur at higher temperatures.

In the subsequent third step, the mixture of the protein-containing solution and transglutaminase is filled in an unillustrated food container at a time t13. In this step, the temperature of the mixture is also maintained at 10–60° C., preferably at 25–50° C., to prevent the catalytic reaction from proceeding by the presence of transglutaminase, which would otherwise occur at higher temperatures.

In the fourth step, the mixture is heated at a low-temperature of 40° C., at a time t14, so as to accelerate the catalytic reaction by transglutaminase, thereby obtaining a protein gel.

In the fifth step, the protein gel is heated at a high-temperature of 90° C., at a time t15, to inactivate transglutaminase.

A protein gel can be manufactured in this manner.

However, in the above-described conventional method of manufacturing a protein gel in which a curdling chemical is used, a mixture of a protein-containing solution and a curdling chemical must be heated at a temperature of 90–95° C. for 30 minutes in the fifth step to curdle the protein-containing solution in the mixture. In another conventional method of manufacturing a protein gel in which transglutaminase is used, a mixture must be first heated at a low temperature of 40° C. in the fourth step to accelerate the catalytic reaction by transglutaminase, and then heated at a high temperature of 90° C. in the fifth step to inactivate the transglutaminase. These conventional methods, therefore, have the drawback that considerable energy is consumed in the manufacturing process, resulting in high manufacturing costs.

An object of the present invention is to solve the problems of the above-described conventional methods of manufacturing a protein gel and to provide a method of manufacturing a protein gel which can reduce the manufacturing costs.

DISCLOSURE OF THE INVENTION

To achieve the object, a method of manufacturing a protein gel according to the present invention includes a first step of heating a protein-containing solution for sterilization, a second step of cooling the protein-containing solution and adding an enzyme thereto, a third step of mixing the protein-containing solution and the enzyme to obtain a mixture, a fourth step of aseptically filling the mixture in a food container, and a fifth step of allowing the aseptically filled mixture to stand at ambient temperature.

The enzyme denatures protein in the protein-containing solution while the mixture is allowed to stand at ambient temperature in the fifth step.

Since the mixture is not required to be heated for denaturing the protein in the protein-containing solution, the energy consumed in the manufacturing process is reduced, thereby lowering the manufacturing costs.

In another method of manufacturing a protein gel according to the present invention, the enzyme is transglutaminase. In this case, the use of the transglutaminase stabilizes the denaturation of protein in the protein-containing solution.

In still another method of manufacturing a protein gel according to the present invention, the amount of the transglutaminase added to the protein-containing solution is determined corresponding to the degree of denaturation of the protein in the protein-containing solution. Accordingly, the amount of transglutaminase can be reduced to the smallest amount which is necessary for the denaturation of protein in the protein-containing solution, thereby lowering the manufacturing costs.

Still another method of manufacturing a protein gel according to the present invention includes a first step of heating a protein-containing solution for sterilization, a second step of cooling the protein-containing solution and adding transglutaminase, magnesium chloride, and calcium lactate thereto, a third step of mixing the protein-containing solution, transglutaminase, magnesium chloride, and calcium lactate to obtain a mixture, a fourth step of aseptically filling the mixture in a food container, and a fifth step of allowing the aseptically filled mixture to stand at ambient temperature.

The transglutaminase, magnesium chloride, and calcium lactate denature protein in the protein-containing solution while the mixture is allowed to stand at ambient temperature in the fifth step.

Since the mixture is not required to be heated for denaturing the protein in the protein-containing solution, the energy consumed in the manufacturing process is reduced, thereby lowering the manufacturing costs.

Also, since the amount of transglutaminase can be reduced by an amount corresponding to the amounts of magnesium chloride and calcium lactate added to the protein-containing solution, the manufacturing costs can be further reduced.

In still another method of manufacturing a protein gel according to the present invention, transglutaminase is added to the protein-containing solution in an amount of 10–40 units with respect to 1 g of protein. Magnesium chloride is preferably added to the solution in a predetermined amount equal to or less than 4.8% by weight with respect to the protein. Calcium lactate is preferably added to the solution in a predetermined amount equal to or less than 1.6% by weight with respect to the protein.

In this case, since the amount of transglutaminase added to the protein-containing solution can be reduced by an amount corresponding to the amounts of magnesium chloride and calcium lactate, the manufacturing costs can be lowered. In addition, since the bitterness of the protein gel caused by magnesium chloride is suppressed, taste of the protein gel can be prevented from being poor. Moreover, since the water-solubility of calcium lactate can be retained, calcium lactate is prevented from being present in the protein gel as a solid matter.

In still another method of manufacturing a protein gel according to the present invention, the temperature of the protein-containing solution in the third step and the temperature of the mixture in the fourth step are maintained at 10–60° C. In this case, the catalytic reaction can be prevented from proceeding in the third and fourth steps.

BEST MODE FOR CARRYING OUT THE INVENTION

Embodiments of the present invention will now be described in detail with reference to the drawings.

Figure 1:
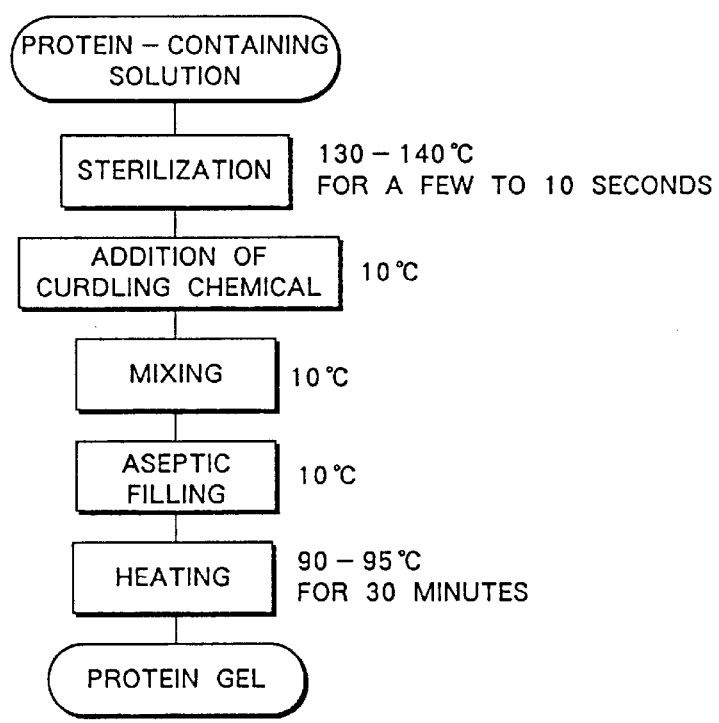
FIG. 1 is a flowchart showing a first conventional method of manufacturing a protein gel.
Figure 2:
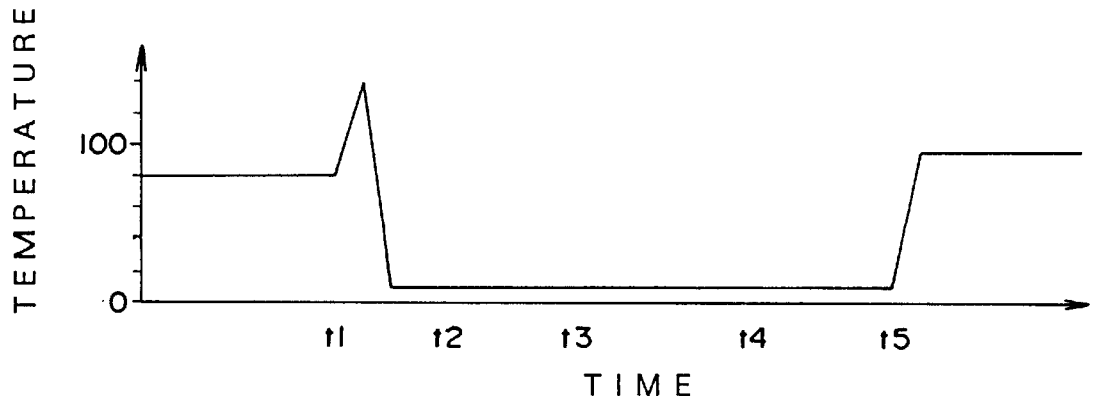
FIG. 2 is a temperature profile in the first conventional method of manufacturing a protein gel.
Figure 3:
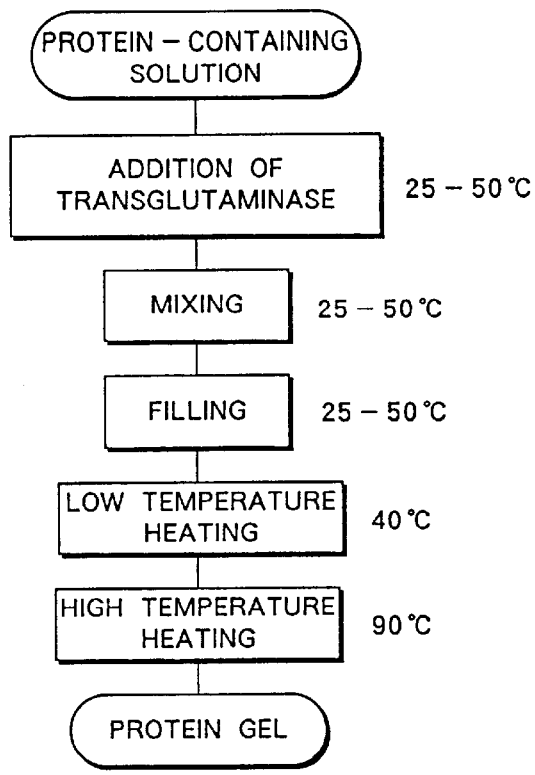
FIG. 3 is a flowchart showing a second conventional method of manufacturing a protein gel.
Figure 4:
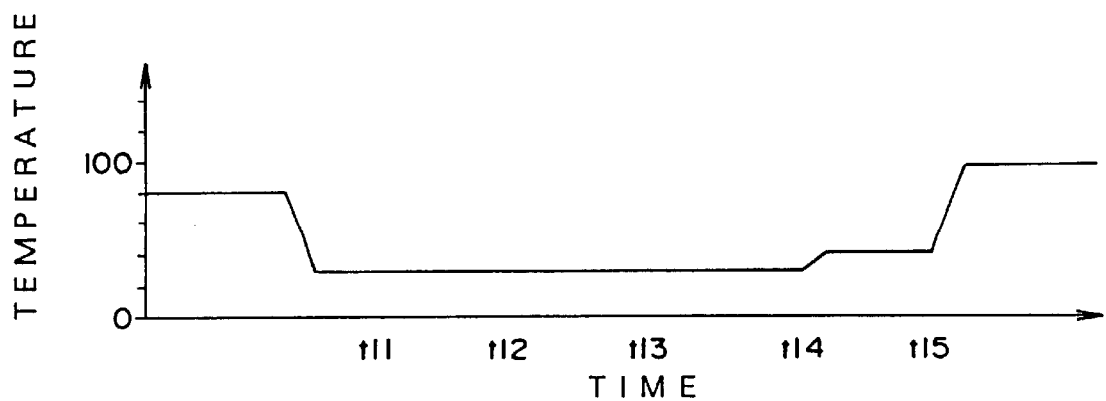
FIG. 4 is a temperature profile in the second conventional method of manufacturing a protein gel.
Figure 5:
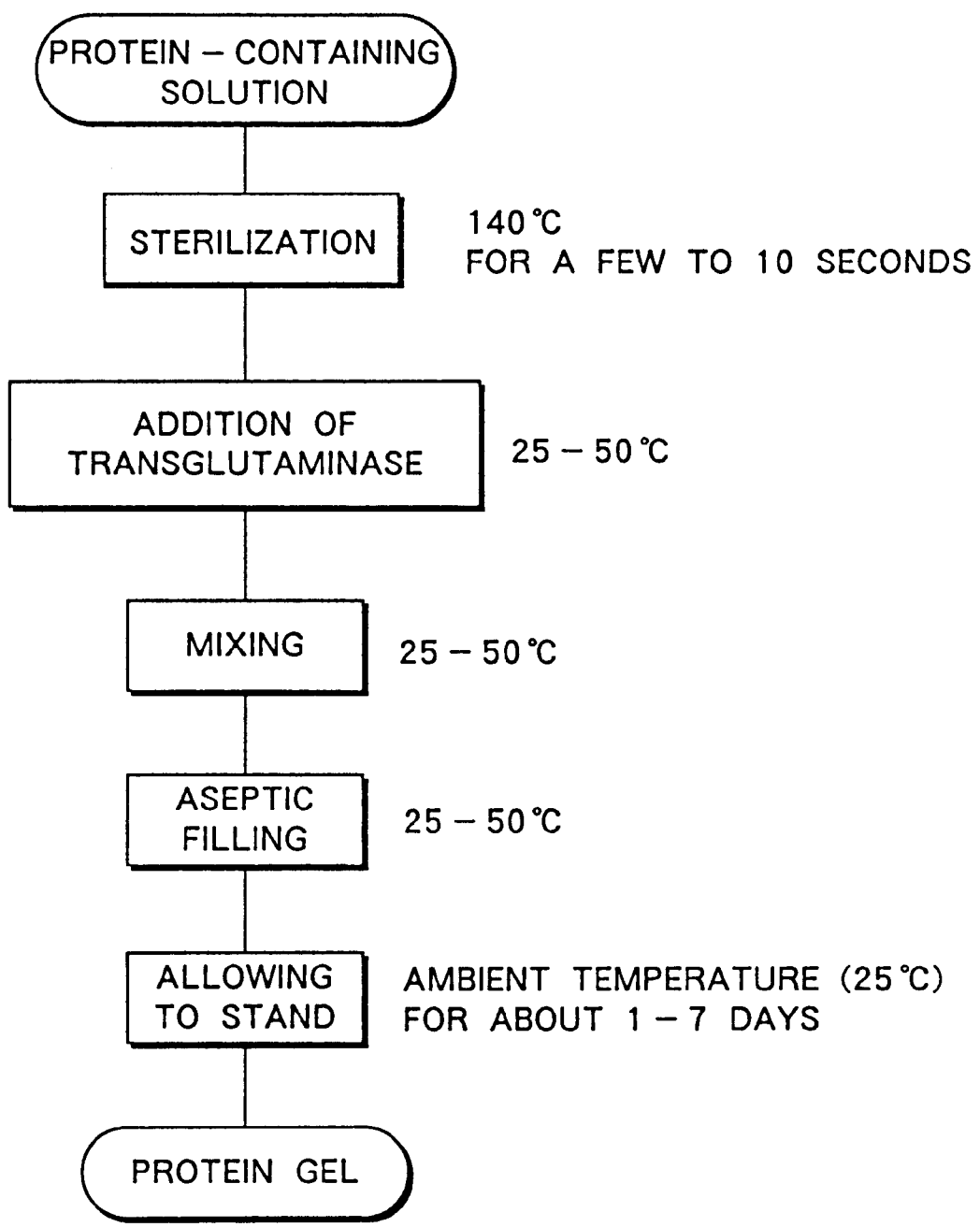
FIG. 5 is a flowchart showing a method of manufacturing a protein gel according to an embodiment of the present invention.
Figure 6:
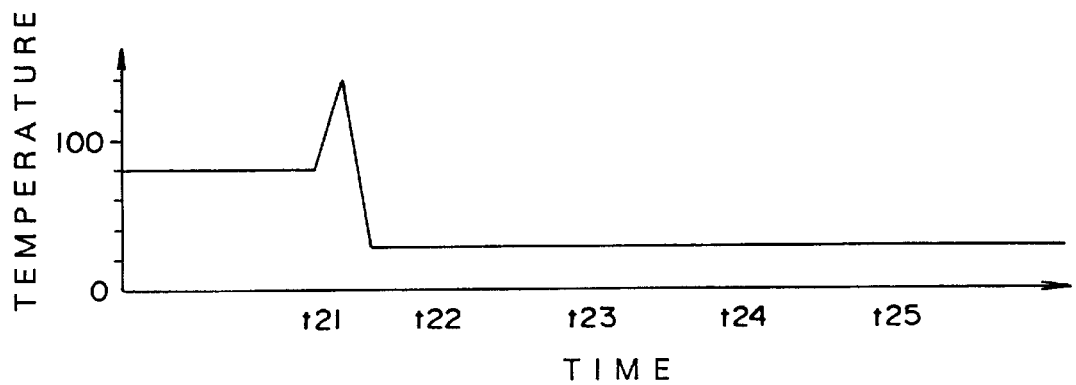
FIG. 6 is a temperature profile in the method of manufacturing a protein gel according to the embodiment of the present invention.

FIG. 5 is a flowchart showing a method of manufacturing a protein gel according to an embodiment of the present invention, and FIG. 6 is a temperature profile in the method of manufacturing a protein gel according to the embodiment of the present invention. In FIG. 6, the abscissa represents time while the ordinate represents temperature.

As shown in FIG. 5, in the first step, the temperature of a protein-containing solution is elevated from about 80° C. to 140° C., at a time t21, to heat the protein-containing solution for a few to 10 seconds for sterilization. The protein-containing solution encompasses slurries, emulsions, paste-like fluids, and the like.

When the protein gel to be obtained is tofu, soymilk is used as the protein-containing solution. First, a process for manufacturing the soymilk will be described. Soy beans are washed and then immersed in an unillustrated immersion tank. Thereafter, the soy beans are crushed with an unillustrated grinder to obtain "go", a paste of crushed soy beans, which is then heated at a temperature of 98–105° C. for 2–5 minutes to denature the protein. Thereafter, tofu refuse is removed from the "go" to obtain soymilk. The denaturation of protein means the phenomenon in which hydrogen bonds, ionic bonds, or part of —S—S bonds in protein are cut so that the regularly aligned protein structure is turned to be a network structure.

In the second step, the protein-containing solution is cooled to a temperature of 10–60° C., preferably of 25–50° C. at a time t22, and then transglutaminase is added to the solution. Transglutaminase is an enzyme serving as a catalyst in an acyl transferring reaction of τ-carboxyamide group, which is a glutamine residue in a peptide chain. Transglutaminase can consistently denature the protein in the protein-containing solution.

In addition to the transglutaminase, other curdling chemicals may be added to the protein-containing solution in an amount of 0.2–0.5% by weight. Examples of such curdling chemicals include acids such as gluconodelta lactone, and divalent cations such as magnesium chloride, calcium sulfate, magnesium sulfate, calcium chloride, etc.

As a result, the amount of transglutaminase can be reduced to lower the manufacturing costs. The amount of transglutaminase can be reduced to the smallest amount which is necessary to curdle protein in the protein-containing solution. The curdling of protein is the phenomenon in which the higher-order structure of denatured protein changes. When the protein in the protein-containing solution denatures, it becomes easier for the above-mentioned divalent cations to enter the protein structure, so that the protein-containing solution starts to curdle.

In the subsequent third step, the protein-containing solution is mixed with the transglutaminase at a time $t23$ to obtain a mixture. In this step, the temperature of the protein-containing solution is maintained at 10–60° C., preferably at 25–50° C., to prevent the catalytic reaction from proceeding, which would otherwise occur at higher temperatures.

In the fourth step, the mixture is aseptically filled in an unillustrated food container at a time $t24$. In this step, the temperature of the protein-containing solution is also maintained at 10–60° C., preferably at 25–50° C., to prevent the catalytic reaction from proceeding by transglutaminase, which would otherwise occur at higher temperatures.

In the fifth step, at a time $t25$, the mixture which has been aseptically filled in the food container is allowed to stand at ambient temperature (for example, 25° C.) for about 1–7 days. The transglutaminase gradually curdles and ripens the protein in the protein-containing solution.

A-protein gel can be manufactured in this way.

In the case where transglutaminase is added to the soymilk to manufacture tofu, 2,000 units (1 activa-TG/source material powder=10,000 units/g) of transglutaminase are needed for 1 g of protein. This results in increased costs.

By adding a predetermined amount of magnesium chloride, and a predetermined amount of calcium lactate in the soymilk, the amount of transglutaminase added to the soymilk can be reduced. If magnesium is added to the soymilk in an amount greater than 6.0% by weight, a strange taste is caused, thereby deteriorating the taste of tofu. If calcium lactate is added to the soymilk in an amount greater than 2.0% by weight, the calcium lactate saturates, so that part of the calcium lactate remains as a solid matter and is caught by the bacteria-removing filter. Also, it gives a granular texture to tofu.

In the present embodiment, 10–40 units of transglutaminase with respect to 1 g of protein, a predetermined amount of 4.8% or less of magnesium chloride (by weight with respect to the total weight of protein), and a predetermined amount of 1.6% or less of calcium lactate (by weight with respect to the total weight of protein) were added to and mixed with the soymilk which was maintained at 10–60° C., preferably at 25–50° C. Thereafter, the mixture of soymilk, transglutaminase, magnesium chloride, and calcium lactate was aseptically filled in a food container and was allowed to stand at 25° C. for 2–5 days. As a result, tofu which was free of strange taste and granular texture was obtained.

Also, in the case where the transglutaminase, magnesium chloride, and calcium lactate were added to and mixed with soymilk, which was maintained at 10–60° C., preferably at 25–40° C., so as to obtain a mixture, and the mixture was then aseptically filled in a food container and was allowed to stand at 25° C. for 2–5 days, fine textured tofu was obtained, which was free of strange taste and granular texture, and in which separation of water was reduced.

In the case where the transglutaminase, magnesium chloride, and calcium lactate were added to and mixed with soymilk maintained at 20° C. so as to obtain a mixture, and the mixture was then aseptically filled in a food container and was allowed to stand at 10° C. or lower for 2–5 days, the soymilk did not curdle.

Next, the properties of a protein gel manufactured by the method of manufacturing a protein gel according to the embodiment of the present invention will be described.

Figure 7:
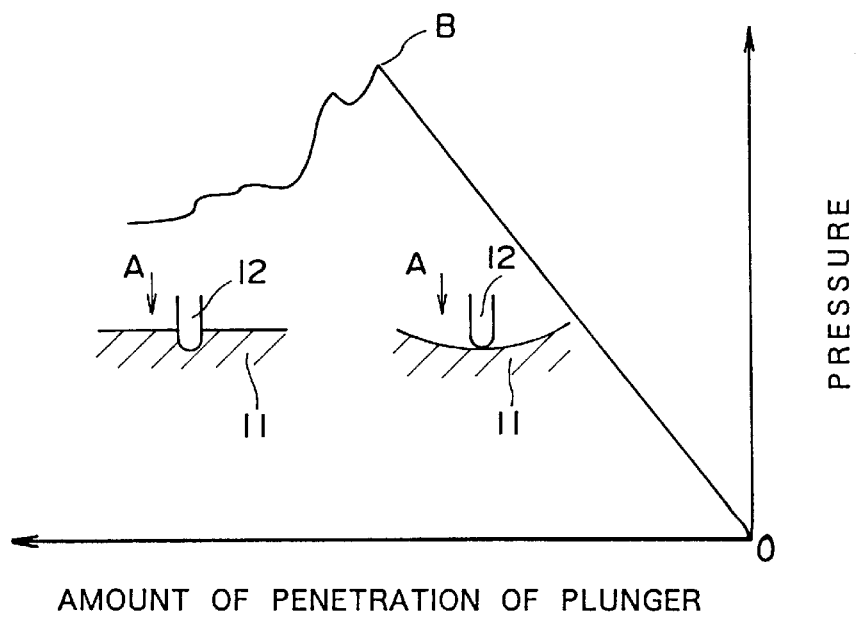
FIG. 7 is a chart showing a gel property of the protein gel according to the embodiment of the present invention.
Figure 8:
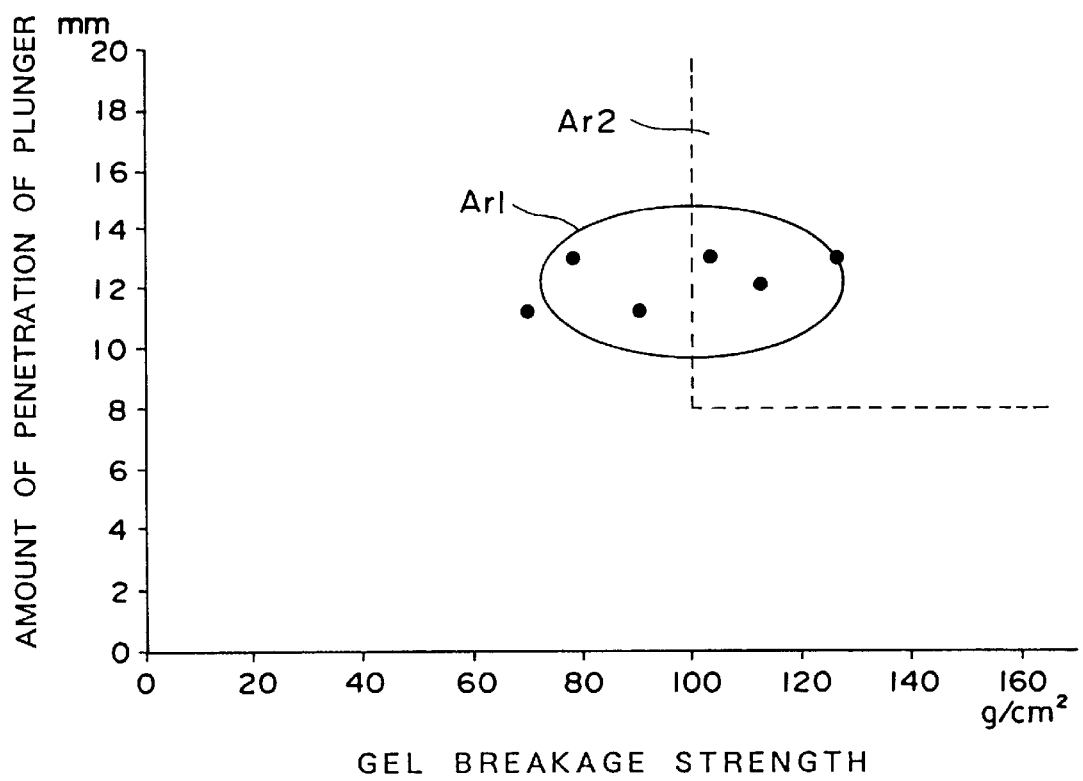
FIG. 8 is a chart showing the strength and gel property of the protein gel.
Figure 9:
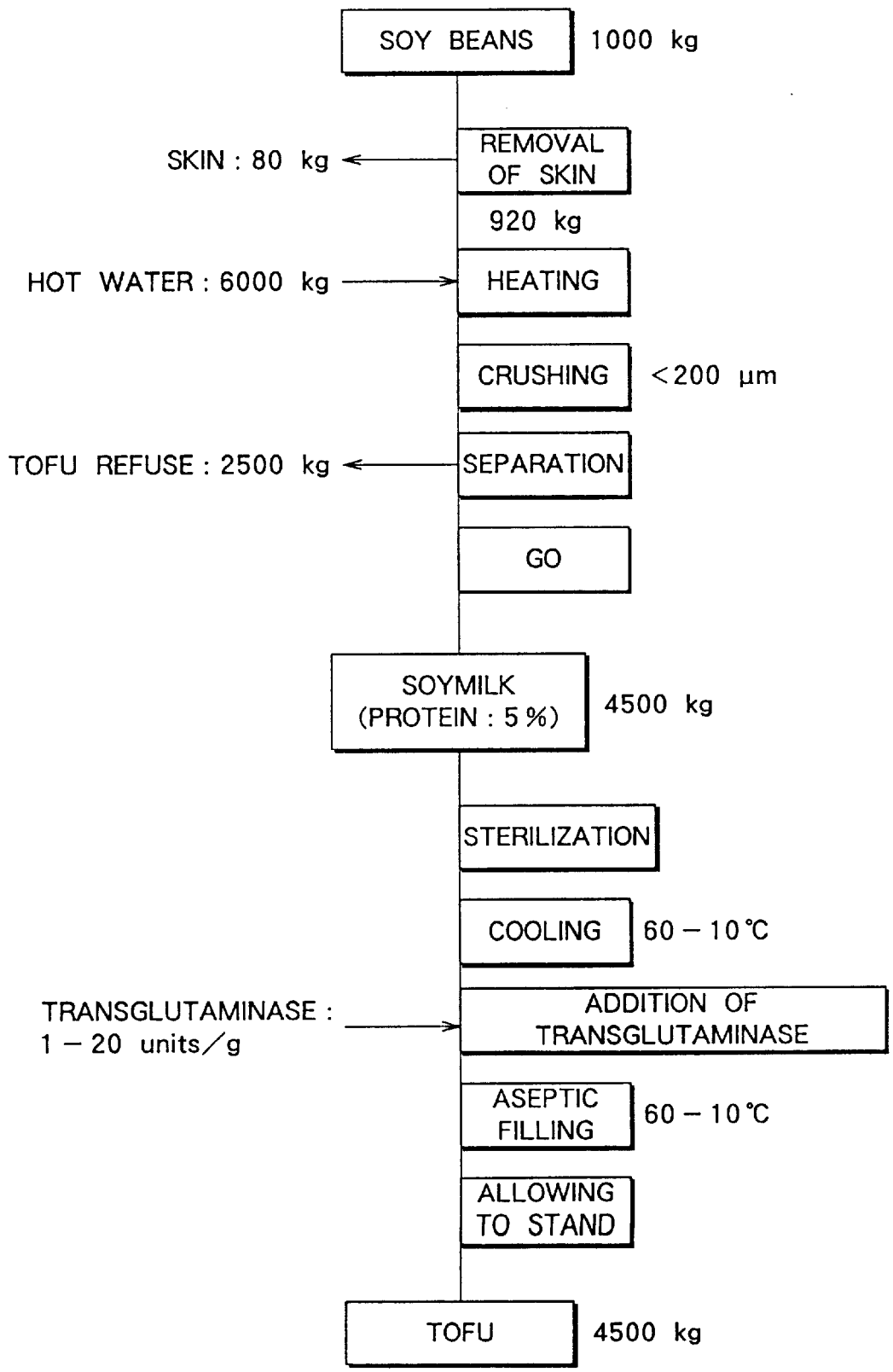
FIG. 9 is a flowchart showing an example of a process for manufacturing a protein gel according to the present invention.

FIG. 7 is a chart showing a gel property of a protein gel according to the embodiment of the present invention, FIG. 8 is a chart showing the strength and gel property of the protein gel, and FIG. 9 is a flowchart showing an example of a process for manufacturing a protein gel according to the present invention. In FIG. 7, the abscissa represents the amount of penetration of a plunger while the ordinate represents the pressure acting on the plunger. In FIG. 8, the abscissa represents pressure at which breakage of gel occurred (hereinafter referred to as "gel breakage strengths") while the ordinate represents the amount of penetration of the plunger.

Tofu 11 was manufactured by the procedure shown in FIG. 9 and its properties were examined. In the manufacture of the tofu 11, 10 units of transglutaminase with respect to 1 g of protein, 4.8% by weight of magnesium chloride, and 1.6%. by weight of calcium lactate were added to soymilk.

As shown in FIG. 7, a plunger 12 having a diameter of 10 mm was disposed perpendicularly to the surface of the tofu 11 and was advanced in the direction indicated by arrow A toward the tofu 11 at a speed of 10 cm/min. The relationship between the pressure applied to the plunger 12 and the amount of penetration of the plunger was examined, using the surface of the tofu as a zero position (0 mm) for the amount of penetration of the plunger.

When the pressure applied to the plunger 12 increased, the tip of the plunger 12 broke the surface of the tofu 11 at a gel breakage point B and entered inside the tofu 11.

When the relationship between the gel breakage strength at the gel breakage point B and the amount of penetration of the plunger was examined for a plurality of pieces of tofu 11 and was plotted, the plotted dots were located within an area Ar1 of FIG. 8. From this, it was revealed that the tofu 11 had a sufficiently high gel breakage strength, and the amount of penetration of the plunger was sufficiently large, compared to conventional tofu.

The area Ar2 of FIG. 8 shows a range in which each dots representing the relationship between the gel breakage strength and the amount of penetration of the plunger were located when the above-described test was performed using tofu 11 manufactured by a conventional method.

The unillustrated food container may be a brick-shaped packaging container. In this case, a web-like packaging material made of a flexible laminated material is sealed in the longitudinal direction to obtain a tubular package in an unillustrated packaging container manufacturing apparatus. The above-described mixture is then aseptically filled in the tubular package, which is sealed in the lateral direction to obtain packaging containers. For example, the packaging material may be the type in which polyethylene film is formed on both sides of a paper substrate as innermost and outermost layers.

When such a packaging container is used as a food container in the conventional method of manufacturing a protein gel, a problem occurs because a mixture must be heated after being filled in the food container. That is, since the polyethylene layer is softened during heating, the sealed portions or the flap portions (triangular tab portions) of the container separates, or the protein gel is set on the polyethylene layer. Also, air or the like dissolved in the mixture expands, so that the food container is deformed. In the case where the food container is immersed in hot water to heat the mixture, water penetrates into the substrate, thereby decreasing the strength of the food container.

By contrast, in the method of manufacturing a protein gel according to the present invention, the mixture is not required to be heated after being filled in the food container. Accordingly, the sealing portions and flap portions of the food container are prevented from separating, and the protein gel is prevented from setting on the polyethylene layer. Also, the food container is not deformed due to expansion of air or the like dissolved in the mixture. In addition, the strength of the food container is prevented from decreasing due to soaking of water into the substrate of the packaging material.

The present invention is not limited to the above-described embodiments, and various modifications and variations can be made based on the spirit of the present invention. Therefore, these modifications and variations should not be construed to be excluded from the scope of the present invention.

INDUSTRIAL APPLICATION

The present invention can be applied to apparatuses for manufacturing a protein gel such as tofu to be filled in a food container.

I claim:

1. A method of manufacturing a tofu protein gel comprising:
    (a) heating a soy protein-containing solution for sterilization;
    (b) cooling said sterilized soy protein-containing solution to a temperature within a range sufficiently low to prevent curdling of the soy protein upon addition of transglutaminase thereto;
    (c) mixing said sterilized soy protein-containing solution and the transglutaminase to obtain a mixture while maintaining the temperature of said sterilized protein-containing solution within said range;
    (d) aseptically filling said mixture in a food container while maintaining the temperature of said sterilized protein-containing solution within said range; and
    (e) reacting the transglutaminase with the soy protein-containing solution at ambient temperature to curdle the soy protein and form the tofu by allowing said aseptically filled mixture to stand in said container at ambient temperature.

2. A method of manufacturing a tofu protein gel according to claim 1, wherein the amount of said transglutaminase added to said protein-containing solution is 10–40 units per 1 g of said soy protein.

3. A method of manufacturing a tofu protein gel comprising:
    (a) heating a soy protein-containing solution for sterilization;
    (b) cooling said soy protein-containing solution to a temperature within a range sufficiently low to prevent curdling of the soy protein upon addition of transglutaminase, magnesium chloride, and calcium lactate thereto;
    (c) mixing said soy protein-containing solution, transglutaminase, magnesium chloride, and calcium lactate to obtain a mixture while maintaining the temperature of said sterilized soy protein-containing solution within said range;
    (d) aseptically filling said mixture in a food container while maintaining the temperature of said sterilized soy protein-containing solution within said range; and
    (e) reacting the transglutaminase, magnesium chloride and calcium lactate with the soy protein-containing solution at ambient temperature to curdle the soy protein and form the tofu by allowing said aseptically filled mixture to stand in said container at ambient temperature.

4. A method of manufacturing a protein gel according to claim 3, wherein said transglutaminase is added to said protein-containing solution in an amount of 10–40 units with respect to 1 g of protein, said magnesium chloride is added to said solution in a predetermined amount equal to or less than 4.8% by weight with respect to the protein, and said calcium lactate is added to said solution in a predetermined amount equal to or less than 1.6% by weight with respect to the protein.

5. A method of manufacturing a protein gel according to claim 1, wherein the temperature of said soy protein-containing solution in the third step and the temperature of said mixture in the fourth step are maintained at 10–60° C.

6. A method according to claim 1 wherein said range is 10–60° C.

7. A method according to claim 1 wherein said range is 25–50° C.

8. A method according to claim 6 wherein said the heating for sterilization is at a temperature of 80–140° C. for no longer than 10 seconds.

9. A method according to claim 1 wherein said heating for sterilization is at 80–140° C. for no longer than 10 seconds.

10. A method according to claim 2 wherein said range is 10–60° C.

11. A method according to claim 2 wherein said range is 25–50° C.

12. A method according to claim 10 wherein said the heating for sterilization is at a temperature of 80–140° C. for no longer than 10 seconds.

13. A method according to claim 11 wherein said the heating for sterilization is at a temperature of 80–140° C. for no longer than 10 seconds.

* * * * *

UNITED STATES PATENT AND TRADEMARK OFFICE
CERTIFICATE OF CORRECTION

PATENT NO. : 5,965,176
DATED : October 12, 1999
INVENTOR(S) : Yoshihisa YAMAMOTO It is certified that error appears in the above-identified patent and that said Letters Patent is hereby corrected as shown below:

Col. 2, line 6, "Y" should read --$\gamma$--.
Col. 4, line 56, "$\tau$" should read --$\gamma$--.

Signed and Sealed this

Nineteenth Day of September, 2000

Attest:

Q. TODD DICKINSON

*Attesting Officer*  *Director of Patents and Trademarks*